United States Patent
Liu et al.

(10) Patent No.: US 10,302,613 B2
(45) Date of Patent: May 28, 2019

(54) ESTIMATION OF CONCENTRATION OF PARTICULATE MATTER IN ATMOSPHERE

(71) Applicant: INTERNATIONAL BUSINESS MACHINES CORPORATION, Armonk, NY (US)

(72) Inventors: Liang Liu, Beijing (CN); Jun Mei Qu, Beijing (CN); Hong Zhou Sha, Beijing (CN); Wei Zhuang, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 60 days.

(21) Appl. No.: 15/290,891

(22) Filed: Oct. 11, 2016

(65) Prior Publication Data

US 2018/0100843 A1 Apr. 12, 2018

(51) Int. Cl.
*G01B 11/14* (2006.01)
*G01N 33/00* (2006.01)

(52) U.S. Cl.
CPC ..... *G01N 33/0062* (2013.01); *G01N 33/0034* (2013.01); *G01N 2033/0068* (2013.01)

(58) Field of Classification Search
USPC .......................................... 701/108; 123/703
See application file for complete search history.

(56) References Cited

U.S. PATENT DOCUMENTS

2015/0285624 A1* 10/2015 Kim ........................ G01B 11/14
348/140
2016/0155027 A1 6/2016 Gong et al.

FOREIGN PATENT DOCUMENTS

WO WO 2011002272 1/2011

OTHER PUBLICATIONS

Zongming Tao, et al., "Profiling the PM2.5 Mass Concentration Vertical Distribution in the Boundary Layer," Atmospheric Measurement Techniques, 9, pp. 1369-1376, 2016.
Chenbin Liu, et al., "Particle pollution estimation based on image analysis," http://journals.plos.org/; Feb. 1, 2016, pp. 1-14.

* cited by examiner

*Primary Examiner* — Lam S Nguyen
(74) *Attorney, Agent, or Firm* — F. Chau & Associates, LLC

(57) ABSTRACT

A computer-implemented method, a computer program product, and a system for adapting a model for estimating a concentration of particulate matter (PM) in the atmosphere includes obtaining image data, humidity data and actual PM concentration data. Visibility is determined from the obtained image data. An estimation model for estimating PM concentration is adapted, based on the determined visibility, the obtained humidity data, and the obtained actual PM concentration data.

19 Claims, 4 Drawing Sheets

ESTIMATION OF CONCENTRATION OF PARTICULATE MATTER IN ATMOSPHERE

BACKGROUND

1. Technical Field

The present disclosure relates to estimation of the concentration of particulate matter in the atmosphere and, more specifically, to estimation of the concentration of particulate matter in the atmosphere based on visibility and humidity.

2. Discussion of the Related Art

Air pollution is a global problem that threatens human health. Air pollution is generally characterized in terms of atmospheric particulate matter (PM). While there are many different types of PM, one important class of PM includes those particles having a particle size that is equal to or less than 2.5 µm. Atmospheric particulate matter of this size may be referred to as "PM2.5" or "$PM_{2.5}$".

In regions where air pollution is of a particular concern, public health officials and individuals may wish to closely monitor PM2.5 concentrations so that during times of relatively high concentrations, the population may be advised to take precautionary measures such as wearing masks and refraining from certain outdoor activities.

BRIEF SUMMARY

A computer-implemented method in accordance with the present invention for adapting a model for estimating a concentration of particulate matter (PM) in the atmosphere includes obtaining image data, humidity data and actual PM concentration data. Visibility is determined from the obtained image data. An estimation model for estimating PM concentration is adapted, based on the determined visibility, the obtained humidity data, and the obtained actual PM concentration data. Other embodiments in accordance with the present invention include a system and computer program product.

BRIEF DESCRIPTION OF THE SEVERAL VIEWS OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION

Figure 1:
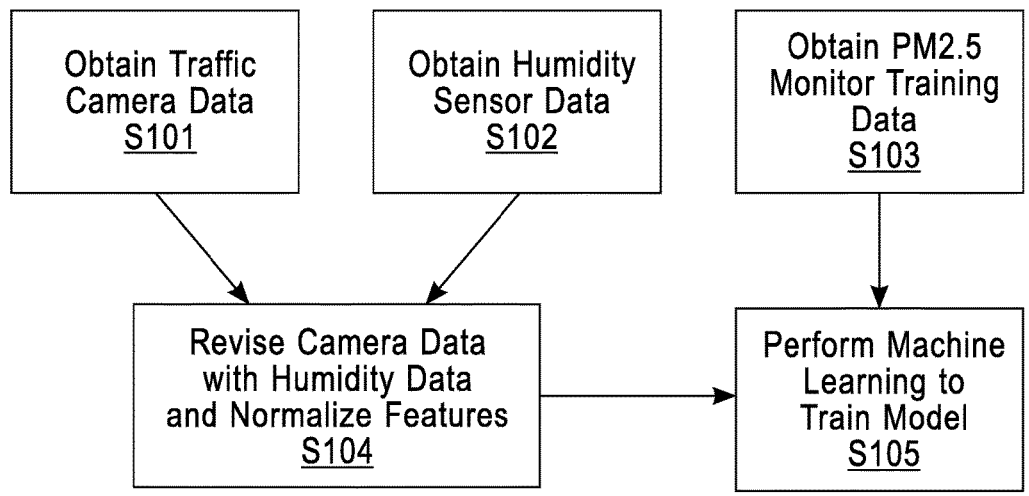
FIG. 1 is a flow chart illustrating an approach for using computer learning to train visibility and humidity-based PM2.5 estimators in accordance with exemplary embodiments of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all equivalents.

Exemplary embodiments of the present invention seek to estimate the concentration of particulate matter in the atmosphere. In a preferred embodiment, the concentration of PM2.5 in the atmosphere is estimated while minimizing the need to utilize expensive PM2.5 monitors. It is noted that even in regions where sophisticated pollution monitoring stations are absent, traffic cameras may still be widely in use. In some embodiments, these traffic cameras may provide a good foundation from which to visually assess air conditions. Exemplary embodiments of the present invention may utilize visual image data, such as that obtained from traffic cameras, to obtain an assessment of air visibility. This visual data is taken along with humidity data that is obtained from humidity sensing instruments such as capacitive humidity sensors, resistive humidity sensors, thermal conductivity humidity sensors, etc. and machine learning is used to take this data along with training data obtained from actual PM2.5 monitors, so that various classifiers may be trained. These trained classifiers may then be applied to real-time air visibility data and humidity data so that PM2.5 concentrations may be subsequently estimated without the use of PM2.5 monitors.

FIG. 1 is a flow chart illustrating an approach for using computer learning to train visibility and humidity-based PM2.5 estimators in accordance with exemplary embodiments of the present invention. As noted above, image data may be acquired, for example, from one or more traffic cameras (S101). Humidity data may also be acquired (S102). By way of example only, the humidity data may be acquired using humidity sensors placed in close proximity to the corresponding traffic cameras, integrated into the traffic cameras, or placed in some other region known to have similar humidity to the area in which the corresponding traffic camera is located. In some situations, it may also be acceptable to use weather report humidity information for the broader region. This weather report information may, for example, be received over the Internet.

However, where humidity data is read directly from humidity sensors, in some embodiments there may be a one-to-one correspondence between each camera and each humidity sensor. Because traffic cameras are rather ubiquitous, they may be easy to fit into the methods described herein, however, other cameras may be used. These cameras may be still picture cameras or video images, and these cameras need not be pointed at roadways.

For the purpose of obtaining training data, a PM2.5 monitor may be used to obtain a PM2.5 concentration reading (S103). The PM2.5 monitor may be used in the vicinity of each of the traffic cameras/humidity sensors so that data triplets of image data, humidity data, and PM2.5 concentration data may be procured.

The image data may then be analyzed to quantify one or more image features that relate to the degree of visibility/degree of haze identified within the image and these features are then normalized with respect to the humidity data (S104), as humidity may tend to affect degree of visibility. In this step, other atmospheric parameters may be considered such as wind speed, dew point, temperature, etc. as these features may also tend to affect degree of visibility. These other atmospheric parameters may be obtained based on instrumentation located in proximity to the cameras or it may be obtained from the weather report data, as described above.

Moreover, by normalizing the image features for humidity, exemplary embodiments of the present invention may be used to estimate PM2.5 concentrations at any level of humidity, rather than having to rely upon an empirical formula for PM2.5 estimation that may only be able to estimate PM2.5 concentrations below a certain humidity threshold, such as 70%. It is noted that as most heavy pollution generally occurs at higher humidity, the approaches of exemplary embodiments of the present invention may be more useful than the empirical formulas.

The PM2.5 concentration data may then be used, along with the revised/normalized image features to train an estimation model using one or more machine learning techniques (S105). In training the model, error back propagation backpropagation (BP) (e.g. the backward propagation of errors) may be used.

Normalization of the visibility features, in S104, may enhance features of the trained estimation model. This normalization may include weighting the visibility features according to humidity. In so doing, a weighting function may be used. The weighting function may serve to reduce the visibility value (e.g. a measure of how much visibility there is) when the humidity is relatively low and increase the visibility value when the humidity is relatively high.

Figure 2:
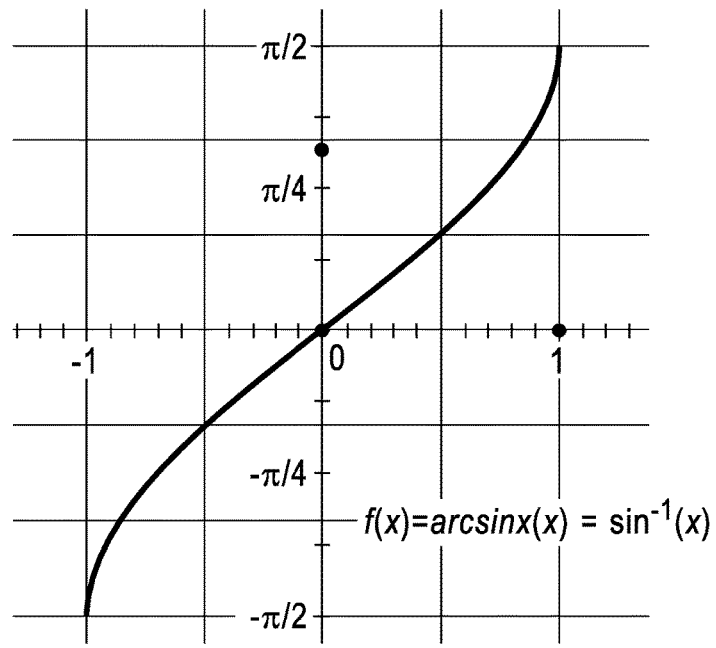
FIG. 2 is a graph illustrating an approach for computing humidity-weighed visibility in accordance with exemplary embodiments of the present invention.

FIG. 2 is a graph illustrating an approach for computing humidity-weighed visibility in accordance with exemplary embodiments of the present invention. In some embodiments, as noted above, the visibility feature of the image data may be weighted according to humidity. Assuming a humidity value within a range of 0 to 100, inclusive, the humidity value may be normalized to within a range of 0 to 1, inclusive. Then, y=arcsin (x) may be introduced to enhance the ability to distinguish between different PM2.5 concentrations, as shown in FIG. 2. The value of visibility may then be normalized. For example, if the equation for visibility (Vis):

$$Vis=Vis \times arcsin(rh/100)$$

is used, where the humidity rh $\in$ the set from 0 to 100, inclusive.

After the estimation model has been trained, for example, as described above, the estimation model may be used to estimate PM2.5 concentration without the use of a PM2.5 monitor.

Figure 3:
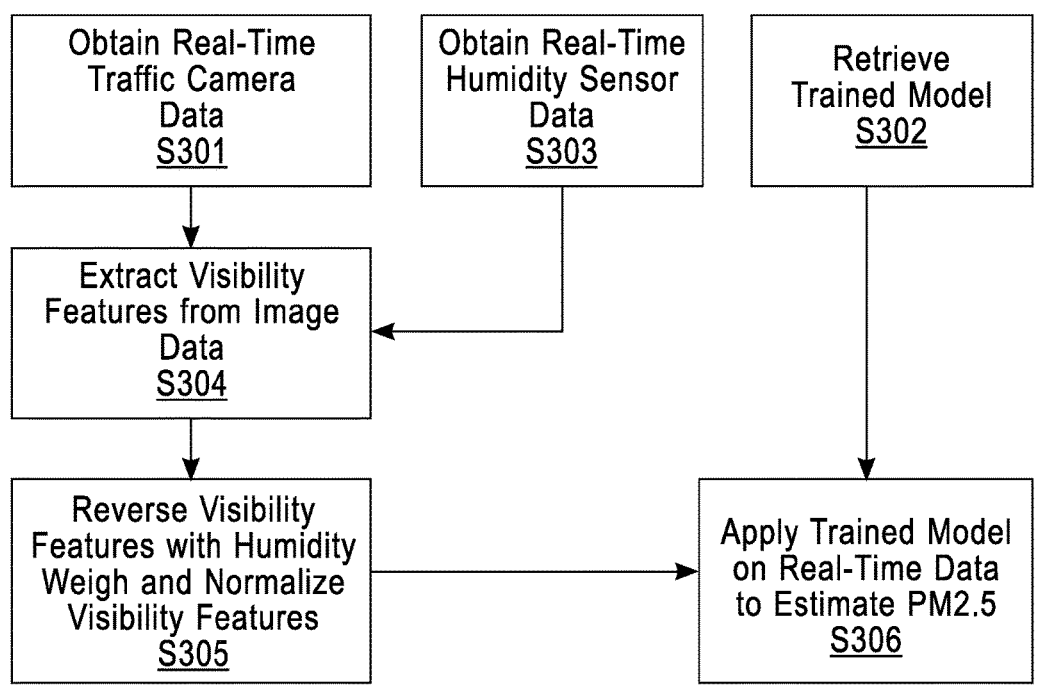
FIG. 3 is a flow chart illustrating an approach for estimating PM2.5 concentration without the use of a PM2.5 monitor in accordance with exemplary embodiments of the present invention.

FIG. 3 is a flow chart illustrating an approach for estimating PM2.5 concentration without the use of a PM2.5 monitor in accordance with exemplary embodiments of the present invention. As depicted, image data is acquired (in S301). Image data may be acquired using traffic cameras, such as noted above. Further, this image data may be acquired in effective real-time, which may mean that as the data is acquired, it may likewise be used to estimate PM2.5 concentrations in effective real time.

Humidity data may also be acquired (in S303) in a manner similar to the approach described above for acquiring humidity data for training purposes. Thus, the humidity data may be acquired using a humidity sensor located in proximity to each traffic camera. The image data may then be analyzed to extract visibility features therefrom (in S304). The extracted visibility features may then be revised in accordance with the obtained humidity data, for example, by performing a weighting process, and the extracted visibility features may be normalized (in S305).

The trained estimation model may be retrieved (in S302) and the retrieved estimation model may then be applied to the normalized and weighted visibility data to generate the PM2.5 concentration estimate (in S306).

Figure 4:
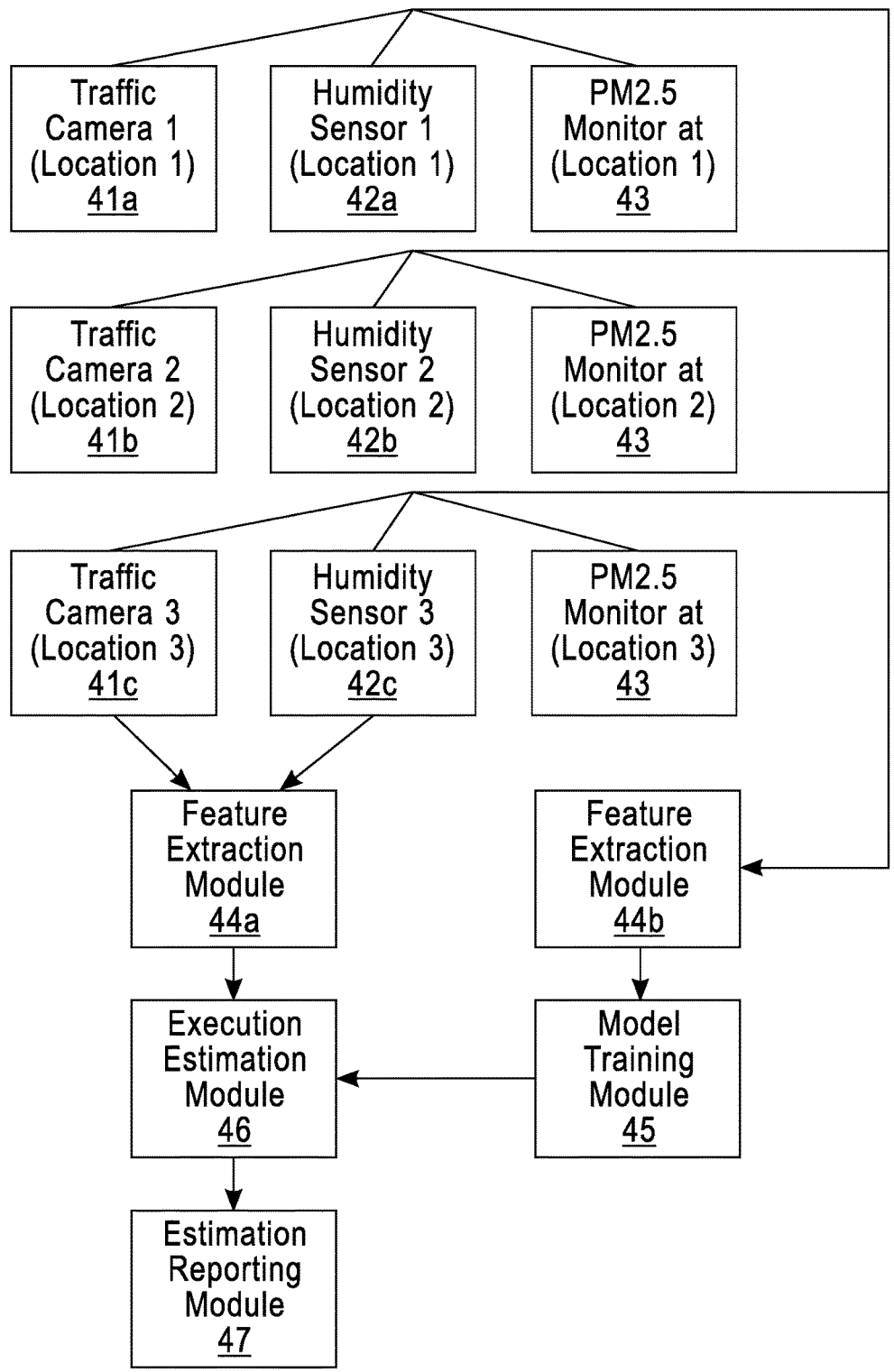
FIG. 4 is a schematic diagram illustrating a system for estimating PM 2.5 concentrations in accordance with exemplary embodiments of the present invention.

FIG. 4 is a schematic diagram illustrating a system for estimating PM 2.5 concentrations in accordance with exemplary embodiments of the present invention. As described above, during the training stage illustrated in FIG. 1, a PM2.5 monitor 43 may be used. However, this monitor 43 need not be permanently installed at the locations 1, 2, and 3 of the traffic cameras 41a, 41b, and 41c. Rather, the PM2.5 monitor 43 may be moved between the three locations (as shown), or training may be performed exclusively at stations where the PM2.5 monitors already exist. It is noted that while some exemplary embodiments of the present invention may train the estimation model using PM2.5 monitor readings acquired at the same locations where the image data is to be acquired in real-time during the monitoring stage of FIG. 2, other exemplary embodiments of the present invention may train the estimation model using PM2.5 monitor readings acquired at different locations from where the image data is to be acquired in real-time during the monitoring stage.

According to the system shown, there may be three traffic cameras 41a, 41b, and 41c, installed at three different locations Location 1, Location 2, Location 3, respectively. Respective humidity sensors Sensor 1 42a, Sensor 2 42b, and Sensor 3 42c may be installed in close proximity to the respective traffic cameras 41a, 41b, and 41c.

In training the estimation model, a feature extraction module 44b may take the data from all of the traffic cameras 41a, 41b, and 41c, along with the data from all of the humidity sensors 42a, 42b, and 42c, and along with the data from the PM2.5 sensor(s) 43, and perform feature extraction therefrom, for example, as described above with respect to FIG. 1. Then a model training module 45 may train the estimation model accordingly, also, for example, as described above with respect to FIG. 1.

A feature extraction module 44a may make use of real-time traffic and humidity sensor data from either the same cameras 41a, 41b, and 41c and humidity sensors 42a, 42b, and 42c, described above, or from different camera and humidity sensor pairs located at different locations.

Then, an execution estimation module 46 may make use of the extracted/normalized/weighted features from the feature extraction module, and the trained model from the model training module 45 and perform real-time estimation therefrom, for example, as described above with respect to FIG. 2.

An estimation reporting module 47 may then be used to issue a report on the PM2.5 concentration estimation, in real-time, and may additionally be used to issue alerts when the PM2.5 concentration estimation exceeds a predetermined threshold.

Figure 5:
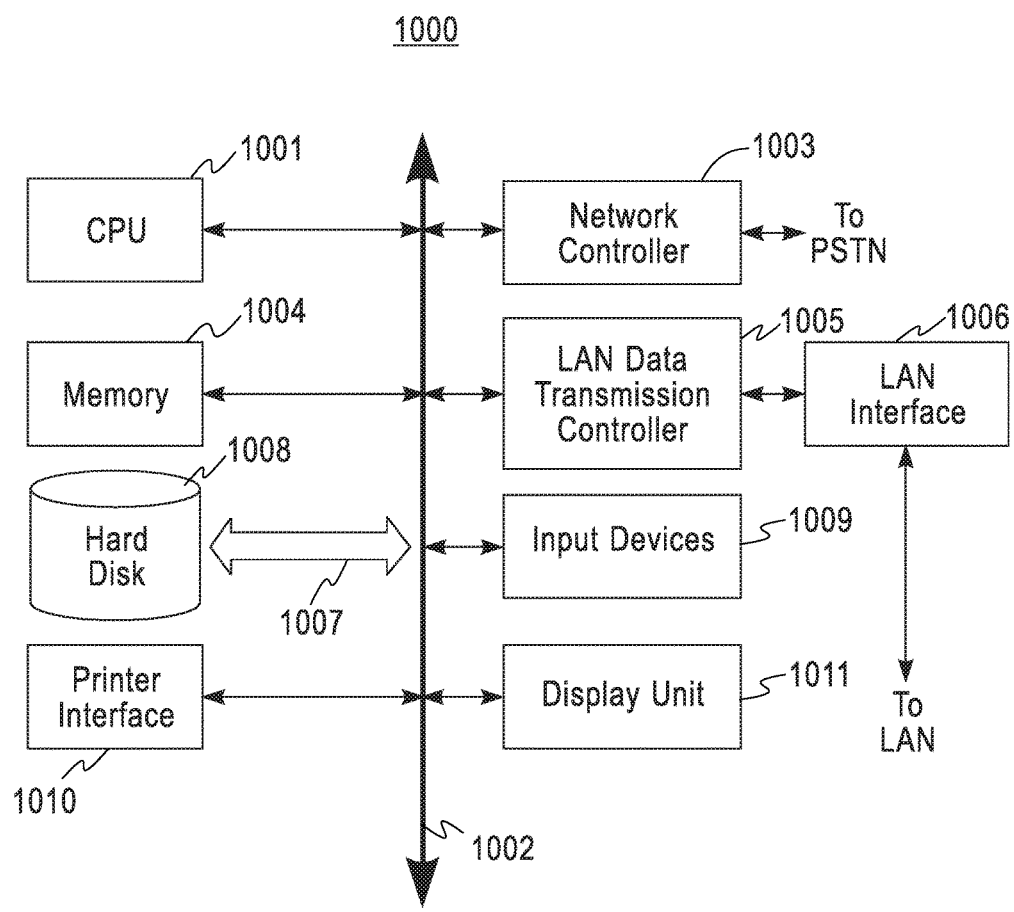
FIG. 5 shows an example of a computer system capable of implementing the method and apparatus according to embodiments of the present disclosure.

FIG. 5 shows an example of a system in accordance with some embodiments of the present invention. By way of overview, some embodiments, the present invention may be implemented in the form of a software application running on a computer system, for example, a mainframe, personal computer (PC), handheld computer, server, etc. The software application may be stored on a computer readable storage media locally accessible by the computer system and/or accessible via a hard wired or wireless connection to a network, for example, a local area network, or the Internet.

Referring now to FIG. 5, a computer system (referred to generally as system 1000) may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A computer-implemented method for adapting a model for estimating a concentration of particulate matter (PM) in the atmosphere, comprising:
   obtaining image data;
   obtaining humidity data;
   determining visibility from the obtained image data;
   obtaining actual PM concentration data; and
   adapting an estimation model, using the obtained actual PM concentration data, for estimating PM concentration from the determined visibility and the obtained humidity data; and
   estimating a subsequent PM concentration, using the adapted estimation model, based on subsequent visibility and humidity data, without the use of subsequent actual PM concentration data.

2. The computer-implemented method of claim 1, further comprising generating an alert when the estimated subsequent PM concentration exceeds a predetermined threshold.

3. The computer-implemented method of claim 1, wherein, in adapting the estimation model based on the determined visibility and the obtained humidity data, the determined visibility is weighted according to the obtained humidity data and the weighted visibility data is used to adapt the estimation model.

4. The computer-implemented method of claim 1, wherein the estimation model is adapted for estimating PM concentration of particulate matter of a size less than or equal to 2.5 μm.

5. The computer-implemented method of claim 1, wherein the image data is obtained at each of a plurality of locations and the humidity data is obtained at each of the plurality of locations.

6. The computer-implemented method of claim 5, wherein the obtaining of the image data at each of the plurality of locations comprises obtaining image data from a plurality of traffic cameras disposed at each of the plurality of locations.

7. The computer-implemented method of claim 5, wherein the obtaining of the humidity data at each of the plurality of locations comprises obtaining image data from a plurality of humidity sensors disposed at each of the plurality of locations.

8. The computer-implemented method of claim 1, wherein the actual PM concentration data is obtained using at least one PM monitor.

9. The computer-implemented of claim 8, wherein the estimation model is adapted for estimating PM concentration of particulate matter of a size less than or equal to 2.5 μm (PM2.5) and the at least one PM monitor is at least one PM2.5 monitor.

10. The computer-implemented method of claim 8, wherein the image data is obtained at each of a plurality of locations, the humidity data is obtained at each of the plurality of locations, and the at least one PM monitor is located at one or more of the locations of the plurality of locations at a time when the actual PM concentration data is obtained.

11. The computer-implemented method of claim 1, wherein the estimation model is adapted using machine learning.

12. The computer-implemented method of claim 11, wherein the machine learning is performed using backpropagation (BP).

13. The computer-implemented method of claim 8, further including, generating an alert when the estimated present PM2.5 concentration exceeds a predetermined threshold.

14. A computer program product for estimating a concentration of particulate matter (PM) in the atmosphere, the computer program product comprising a computer readable storage medium having program instructions embodied therewith, the program instructions executable by a computer to cause the computer to:
   receive, by the computer, image data;
   receive, by the computer, humidity data;
   determine, by the computer, visibility from the received image data;
   receive, by the computer, actual PM concentration data;
   adapt, by the computer, an estimation model, using the obtained actual PM concentration data, for estimating PM concentration from the determined visibility and the received humidity data; and
   estimate, by the computer, a subsequent PM concentration, using the adapted estimation model, based on subsequent visibility and humidity data, without the use of subsequent actual PM concentration data.

15. The computer program product of claim 14, wherein the program instructions executable by a computer additionally to cause the computer to:
   generate an alert, by the computer, when the estimated subsequent PM concentration exceeds a predetermined threshold.

16. The computer program product of claim 14, wherein in adapting the estimation model based on the determined visibility and the received humidity data, the determined visibility is weighted according to the received humidity data and the weighted visibility data is used, by the computer, to adapt the estimation model.

17. The computer program product of claim 14, wherein the estimation model is adapted, by the computer, for estimating PM concentration of particulate matter of a size less than or equal to 2.5 μm.

18. The computer program product of claim 14, wherein the estimation model is adapted, by the computer, using backpropagation (BP) machine learning.

19. A system for estimating a concentration of particulate matter (PM) in the atmosphere, comprising:
   at least one processor;
   a memory, operably coupled to the at least one processor;
   a first camera for obtaining first image data; a first humidity sensor for obtaining first humidity data;
   a PM monitor for obtaining actual PM concentration data;
   a first processor for determining a first visibility from the obtained first image data, adapting an estimation model, using the obtained actual PM concentration data, for estimation PM concentration from the determined first visibility and the obtained first humidity data, and estimating a subsequent PM concentration, using the adapted estimation model, based on subsequent visibility and humidity data, without the use of subsequent actual PM concentration data.

* * * * *